US009925399B1

(12) United States Patent
Goldberg

(10) Patent No.: US 9,925,399 B1
(45) Date of Patent: Mar. 27, 2018

(54) EMERGENCY AVALANCHE BREATHING DEVICE

(71) Applicant: Sophie Rose Goldberg, Denver, CO (US)

(72) Inventor: Sophie Rose Goldberg, Denver, CO (US)

(*) Notice: Subject to any disclaimer, the term of this patent is extended or adjusted under 35 U.S.C. 154(b) by 0 days.

(21) Appl. No.: 15/446,994

(22) Filed: Mar. 1, 2017

(51) Int. Cl.
*A62B 33/00* (2006.01)
*A62B 9/06* (2006.01)
*A62B 7/12* (2006.01)
*A62B 25/00* (2006.01)
*A61M 15/00* (2006.01)
*A61M 16/00* (2006.01)
*A61M 16/04* (2006.01)
*A61M 25/02* (2006.01)

(52) U.S. Cl.
CPC ......... *A62B 33/00* (2013.01); *A61M 15/0023* (2014.02); *A61M 16/049* (2014.02); *A61M 16/0488* (2013.01); *A62B 7/12* (2013.01); *A62B 9/06* (2013.01); *A62B 25/00* (2013.01); A61M 2025/022 (2013.01); A61M 2210/0625 (2013.01)

(58) Field of Classification Search
CPC ......... A62B 33/00; A62B 18/00; A24F 13/12; A45B 2009/007; A45B 2200/055; A45B 3/00; A45B 9/00; A61F 2/95; A61F 2/962; A61M 16/0057; A61M 16/06; A61M 16/0622; A61M 16/0633; A61M 16/0816; A61M 16/0875; A61M 2205/0216; A61M 25/0052; A63B 2024/0025; A63B 2207/02; A63B 2220/836; A63B 2225/50; A63B 24/0021; A63B 29/021; A63B 47/02; A63B 55/10; A63C 11/221; A63C 11/225; B63C 11/205; F16B 7/14; F16B 3/13; Y10T 403/32426
USPC ............ 128/200.24, 201.11, 201.22, 201.27, 128/201.28, 202.13, 207.14
See application file for complete search history.

(56) References Cited

U.S. PATENT DOCUMENTS 6,079,410 A * 6/2000 Winefordner ......... B63C 11/205
128/201.11
6,270,386 B1 * 8/2001 Visocekas ............ A41D 13/018
441/104
8,393,328 B2 * 3/2013 Angel .................... A61M 16/04
128/200.26

(Continued)

FOREIGN PATENT DOCUMENTS

CA 2420627 A1 8/2004
DE 19643265 A1 * 1/1998 ............. A62B 33/00

*Primary Examiner* — Annette Dixon
(74) *Attorney, Agent, or Firm* — Holland & Hart LLP

(57) ABSTRACT

An emergency breathing apparatus for use in case of burial by an avalanche is described. The breathing apparatus may include a telescoping body configured to transition between a collapsed and extended configuration. The body may include a plurality of tubular members. The breathing apparatus may include a breathing port on one end of the device, a plurality of apertures on the opposite end of the device, and an internal lumen that fluidly connects the breathing port with the plurality of apertures. The breathing apparatus may include a spring assembly, a motorized extension mechanism, a pneumatic extension mechanism, or a combination of these devices, that are configured to extend the body from a collapsed configuration to an extended configuration.

12 Claims, 6 Drawing Sheets

(56) References Cited

U.S. PATENT DOCUMENTS

| | | | |
|---|---|---|---|
| 9,216,264 B2 * | 12/2015 | Ho | A61M 16/06 |
| 9,744,325 B2 * | 8/2017 | Ho | A61M 16/0622 |
| 2005/0126565 A1 * | 6/2005 | Huang | A62B 33/00 |
| | | | 128/202.13 |
| 2007/0157925 A1 * | 7/2007 | Shterenberg | A62B 18/00 |
| | | | 128/200.24 |
| 2009/0173342 A1 | 7/2009 | Hamilton | |
| 2012/0138741 A1 * | 6/2012 | Fabre | G01S 5/0231 |
| | | | 244/1 R |

* cited by examiner

EMERGENCY AVALANCHE BREATHING DEVICE

FIELD OF TECHNOLOGY

The present disclosure relates generally to an emergency breathing device used in the case of burial by an avalanche.

BACKGROUND

Due to the growing popularity of backcountry winter sports, deaths caused by avalanches are increasing. In most cases, a victim caught in an avalanche dies from asphyxiation due to burial in snow rather than trauma or the impact of the avalanche itself. Therefore, providing oxygen to the victim pending rescue is crucial to increasing the chances of survival. Existing emergency breathing devices may extract oxygen from the surrounding snow or from an air tank. However, such devices can be prone to failure, bulky, and expensive, or provide access to oxygen for a limited time, therefore reducing their utility to the average user.

DETAILED DESCRIPTION

For a person buried by an avalanche, the most serious threat of death is running out of oxygen before being rescued. Existing emergency breathing devices extract oxygen from the surrounding snow or from an air tank worn by the user. However, such devices may be prone to failure, bulky, or expensive, or provide access to oxygen for a limited time. As such, users may not choose to purchase or use these devices.

In accordance with aspects of the present disclosure, a breathing device is described that provides a breathing passageway from the buried victim to the surface of the snow so the victim can breathe until they are rescued. The described device may be compact, lightweight, reliable, and relatively inexpensive in comparison to existing devices described above. The breathing device may be configured to transition between a collapsed and extended configuration.

In the collapsed configuration, the breathing device may be easily worn by a user strapped across the chest or on the hip, for example. If the user is buried by snow in an avalanche, the user can extend the breathing device up through the snow to the surface, thereby providing a breathing passageway to the surface that could offer indefinite access to oxygen.

In some examples, the breathing device includes a plurality of tubular members configured to collapse and extend in a telescoping manner. The breathing device may include a breathing port on the proximal end of the device (e.g., the end closet to the user), a plurality of holes through one or more of the tubular members near the distal end of the device (e.g., the end farthest from the user), and a lumen connecting the breathing port to the plurality of holes. Once the device has been extended up through the snow, the user may place their mouth on the breathing port and draw air through the plurality of holes.

As described in more detail below, the breathing device may be configured to transition from a collapsed configuration to an expanded configuration in a number of ways. In some examples, the breathing device includes a spring assembly configured to extend the body of the device. In other examples, the breathing device includes a motorized mechanism (e.g., a linear actuator) configured to extend the device. In yet other examples, the breathing device includes a pneumatic extension mechanism configured to extend the device by releasing compressed air. These examples are intended to be non-limiting and other devices or methods may be used to extend the breathing device from a collapsed configuration.

Figure 1A:
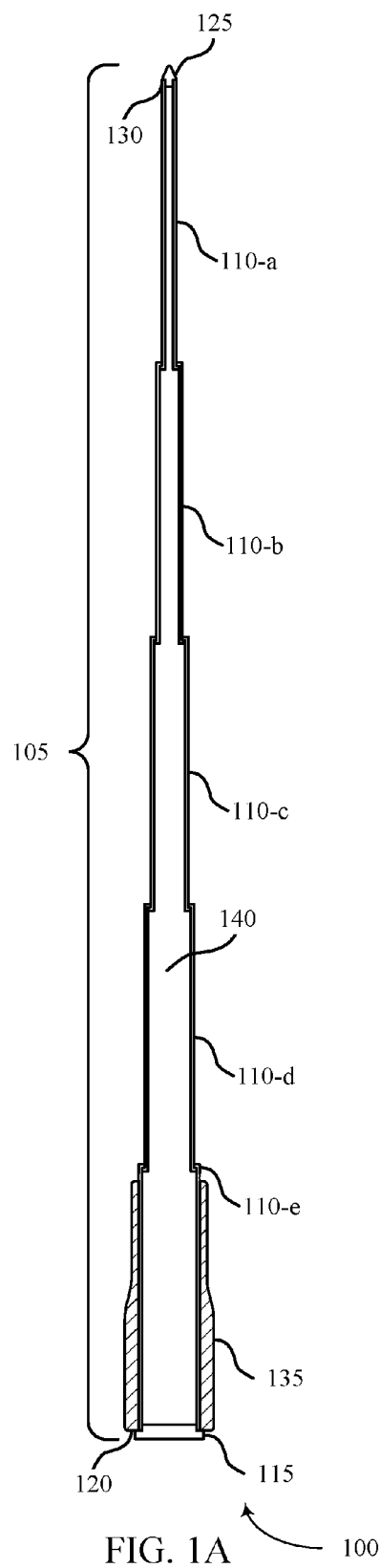
FIG. 1A illustrates an example of a breathing apparatus in an expanded configuration in accordance with aspects of the present disclosure.
Figure 1B:
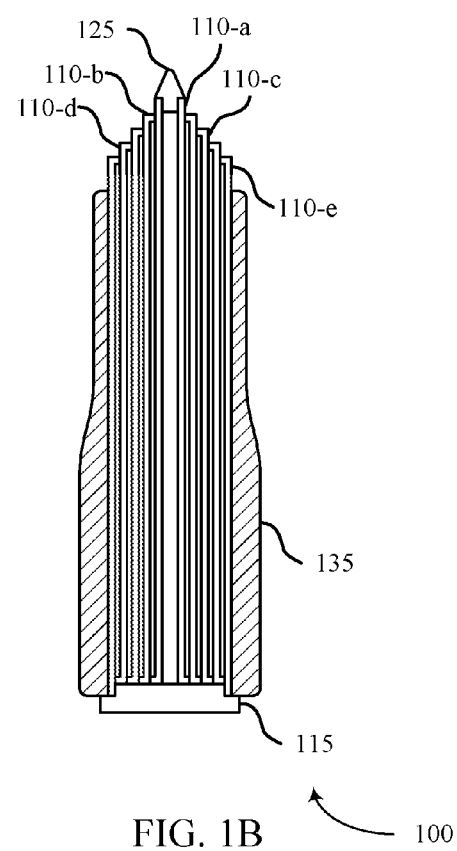
FIG. 1B illustrates an example of a breathing apparatus in a collapsed configuration in accordance with aspects of the present disclosure.

FIG. 1A illustrates an example of a breathing device 100 in an expanded configuration in accordance with various aspects of the present disclosure. FIG. 1B illustrates the breathing device 100 in a collapsed configuration. The breathing device 100 may include a telescoping body 105 configured to transition between the collapsed configuration and the expanded configuration. The body 105 may include a plurality of tubular members 110 configured to slidably couple with each other to facilitate the telescoping motion of the body 105. The tubular members 110 may be generally hollow. The diameter of tubular member 110-e is greater than the diameter of tubular member 110-d, which is greater than the diameter of tubular member 110-c, etc. Although five tubular members 110 are illustrated in this example, it may be appreciated that more or less tubular members 110 may be used to form the telescoping body 105.

The tubular members 110 may be made from any suitable material (e.g., aluminum, plastic, composite material) that provides sufficient rigidity to pierce through snow while being relatively lightweight. The tubular members 110 may be assembled in any way to accommodate a telescoping motion. For example, each tubular member 110 may include an external ledge on the proximal end and an internal ledge on the distal end that act as stops for coupling with the adjacent tubular members 110.

The breathing device 100 may also include a breathing port 115 at or near the proximal end 120 of the body 105. The breathing port 115 generally provides access to the internal lumen 140. In some examples, the breathing port 115 may be shaped to accommodate a human mouth. The breathing port 115 may also include a flexible tubular section that extends away from the body 105.

The breathing device 100 may also include a tip 125 at or near the distal end 130 of the body 105. The tip may be fixedly coupled with the distal most tubular member 110 (e.g., tubular member 110-a). The tip 125 may be made from any suitable material (e.g., aluminum, plastic, composite material), and may be sharpened to a point to facilitate piercing through dense snow or ice. As described in more detail below, the tip 125 may include other features to assist in rescuing the person buried in an avalanche, such as a bright flashing light, an exploding dye pack, a GPS beacon, a speaker, etc.

The body 105 may also include a handle 135 coupled with a tubular member 110 (e.g., tubular member 110-e) at or near the proximal end 120. The handle 135 may include gripping features (e.g., ridges, bumps, etc.) to enhance grip. In some examples, the handle 135 is generally tubular, as illustrated in FIG. 1A. In other examples described in more detail below, the handle 135 may be shaped as a pistol handle to further improve grip and user manipulation.

The dimensions of the body 105 and tubular members 110 may vary depending on the application. In many cases, the average depth of snow burial from an avalanche is typically less than around 100 centimeters (cm). Therefore, in one example, the body 105 may have a total length of 125 cm, where each tubular member 110 has a length of 25 cm.

The breathing device 100 may include a plurality of apertures (shown in detail in FIG. 2) in at least one of the tubular members 110 (e.g., in tubular member 110-a). These apertures may allow air to pass between outside the body 105 and the internal lumen 140 within the body 105. The apertures may be in the form of holes drilled through the wall of one or more of the tubular members 110.

The internal lumen 140 may provide an air passageway between the breathing port 115 and the plurality of apertures. The internal lumen 140 may be formed from the hollow space of the tubular members 110, or may be made from a separate tube running the length of the body 105 and connecting the breathing port 115 to the apertures.

As described in more detail below, the breathing device 100 may include a device or assembly of devices configured to extend the body 105. For example, the breathing device 100 may include a single spring, a spring assembly, a motorized assembly, or a combination of these devices. Extension of the body 105 may be triggered by a user by releasing a latch, pulling a trigger, pressing a button, pulling a cord, tearing a membrane, or some other similar action.

The breathing device 100 may generally be stored and carried in the collapsed configuration shown in FIG. 1B. As described in more detail below, the body 105 may be restrained in a collapsed configuration by a latching mechanism. The breathing device 100 may be sized to be carried across the chest or around the waist of a user and may include other features to conveniently attach and detach from the user (e.g., a holster, a strap, a Velcro® tab, etc.). The collapsibility of the breathing device 100 combined with the lightweight construction of the body 105 may increase the convenience and utility of the breathing device 100 for use by a wide range of users (e.g., skiers, hikers, emergency responders, etc.)

To use the breathing device 100 (e.g., in the case of being buried by snow from an avalanche), a user may extend the body 105 from the collapsed configuration to an expanded configuration. In some examples, the user may release a latch thereby allowing an internal spring assembly to fully extend the body 105. In other cases, the user may trigger a motor to extend the body 105. Regardless of the mechanism used to extend the body 105, once extended above the surface of the snow, the user may breathe through the breathing port 115 to draw air through the apertures and down through the internal lumen 140. as long as the apertures extended above the snow.

Figure 2:
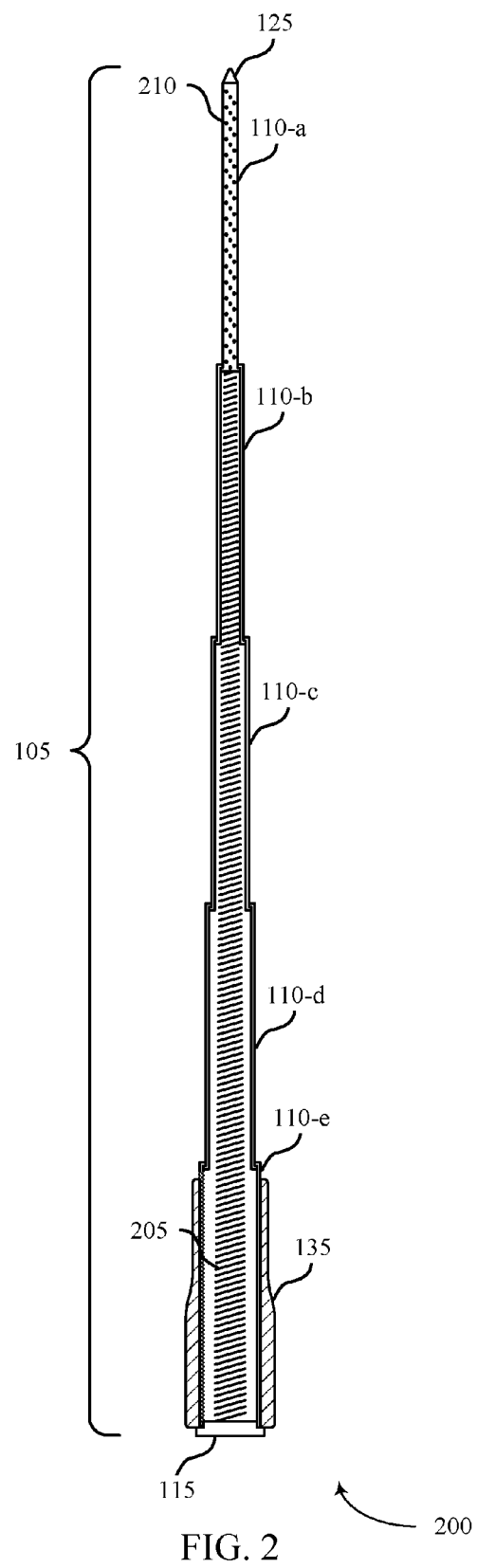
FIG. 2 illustrates an example of a breathing apparatus with a single spring in accordance with aspects of the present disclosure.

FIG. 2 illustrates an example of a breathing device 200 in an expanded configuration in accordance with aspects of the present disclosure. The breathing device 200 may be an example of or include features of the breathing device 100 illustrated with reference to FIG. 1. The breathing device 200 may include a spring assembly 205 disposed within the body 105. The spring assembly 205 may be configured to extend the body 105 from a collapsed configuration to an expanded configuration. The spring assembly 205 may include a single spring or a plurality of springs joined together.

In some examples, the spring assembly 205 includes a single conically-tapered compression spring. In such cases, the diameter of the spring assembly 205 near the proximal end of the body 105 is greater than the diameter of the spring assembly 205 near the distal end of the body 105. As illustrated, the length of the spring assembly 205 may be selected to extend through tubular members 110-e, 110-d, 110-c, and 110-b. As such, the spring assembly 205 may be configured to push on a proximal end of tubular member 110-a, thereby extending it from tubular member 110-b, which extends from tubular member 110-c, etc, until the body 105 is fully extended. As illustrated in this example, the spring assembly 205 may not extend into tubular member 110-a. However, in other examples, the spring assembly 205 may extend through tubular member 110-a and push on the distal end of tubular member 110-a. It should be appreciated that the length, coil dimensions, and material properties of the spring assembly 205 may be selected to provide sufficient pushing force to drive the tip 125 through approximately 100 cm of dense snow.

In other cases, the spring assembly 205 includes a plurality of cylindrical springs of various diameters joined together to form a single conically tapered spring. The plurality of cylindrical springs may be joined end-to-end (e.g., by welding or some other form of adhesion). In other examples, the plurality of cylindrical springs may be threaded to each other (e.g., the distal end of one spring may be threaded into the proximal end of the adjacent spring having a slightly larger diameter).

As illustrated in FIG. 2, the tapering diameter of the spring assembly 205 may be selected to gradually reduce in accordance with the gradual reduction in diameter of the tubular members 110. As described above, the tapering diameter of the spring assembly 205 may be accomplished with a single conically tapered spring or a plurality of cylindrical springs joined together. Using a conically tapered spring assembly may provide a larger average spring diameter than if a single cylindrical spring was chosen with a diameter small enough to accommodate the smallest tubular member 110 (e.g., tubular member 110-b). Therefore, a conically tapered spring may provide an increased spring force as compared to a single cylindrical spring.

The breathing device 200 may also include a plurality of apertures 210 disposed on the tubular member 110-a. Although the apertures 210 are shown on tubular member 110-a, in some examples, the apertures 210 may also be on one or more additional tubular members 110. The apertures 210 may be spaced with respect to each other in any suitable pattern (e.g., randomly placed, spiral configuration, equally spaced, a plurality of rings, etc.). In general, the apertures 210 provide airflow from outside the body 105 to an internal lumen (not shown here for clarity). The shape of the apertures 210 may be cylindrical, square, oval, or any other suitable shape. The size and number of the apertures 210 may be selected to provide sufficient airflow for a human to breath. In some examples, the apertures 210 may include features to prevent snow from getting into the internal lumen, such as one-way valves.

Figure 3:
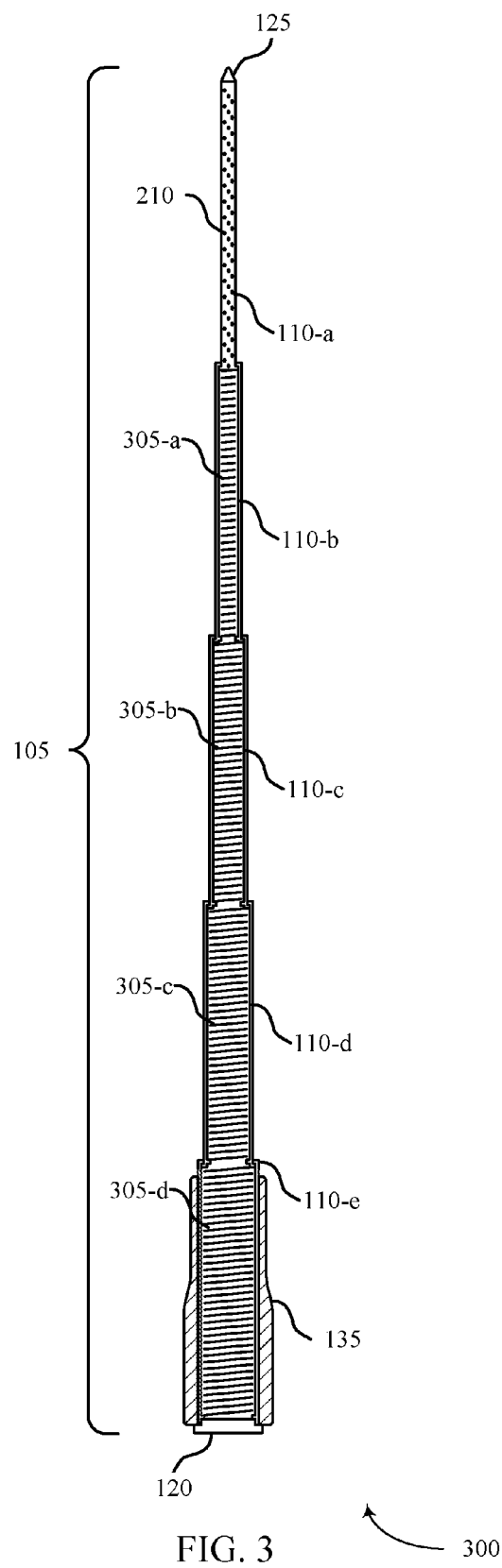
FIG. 3 illustrates an example of a breathing apparatus with multiple springs in accordance with aspects of the present disclosure.

FIG. 3 illustrates an example of a breathing device 300 in an expanded configuration in accordance with aspects of the present disclosure. The breathing device 300 may be an example of or include features of breathing device 100 or 200 described with reference to FIGS. 1 and 2. The breathing device 300 may include a plurality of springs 305. Each spring 305 may be disposed within a single tubular member 110. For example, spring 305-d may be disposed within tubular member 110-e and spring 305-c may be disposed within tubular member 110-d, etc. As illustrated, the number of springs 305 may be one less than the number of tubular members 110.

The springs 305 may be cylindrical in shape. The diameter of each spring 305 may be selected to be slightly smaller than the inner diameter of the corresponding tubular member 110. Using springs 305 that closely match the diameter of the tubular members 110 within which they are disposed may provide a greater average spring diameter for the breathing device 300 than if a conically tapered spring were used. Also, using individual springs 305 may allow customization of the spring material and coil dimensions for each tubular member 110. For example, because the diameter of spring 305-a is smaller than the diameter of spring 305-d, the material selected for spring 305-a may be stiffer than the material selected for spring 305-d, which may allow the spring forces exerted by each spring to be similar.

As illustrated, the springs 305 may not be directly coupled with each other. Instead, each spring 305 may rest on a ledge or lip of its corresponding tubular member 110 and press against the bottom (e.g., proximal end) of the adjacent tubular member 110 that is smaller in diameter. For example, spring 305-d may rest on an internal ledge near the proximal end of tubular member 110-e and press against the proximal end of tubular member 110-d. Similarly, spring 305-c may rest on an internal ledge near the proximal end of tubular member 110-d and press against the proximal end of tubular member 110-c. In this way, each spring 305 acts to extend one tubular member 110 from the tubular member 110 from which it is disposed.

Figure 4:
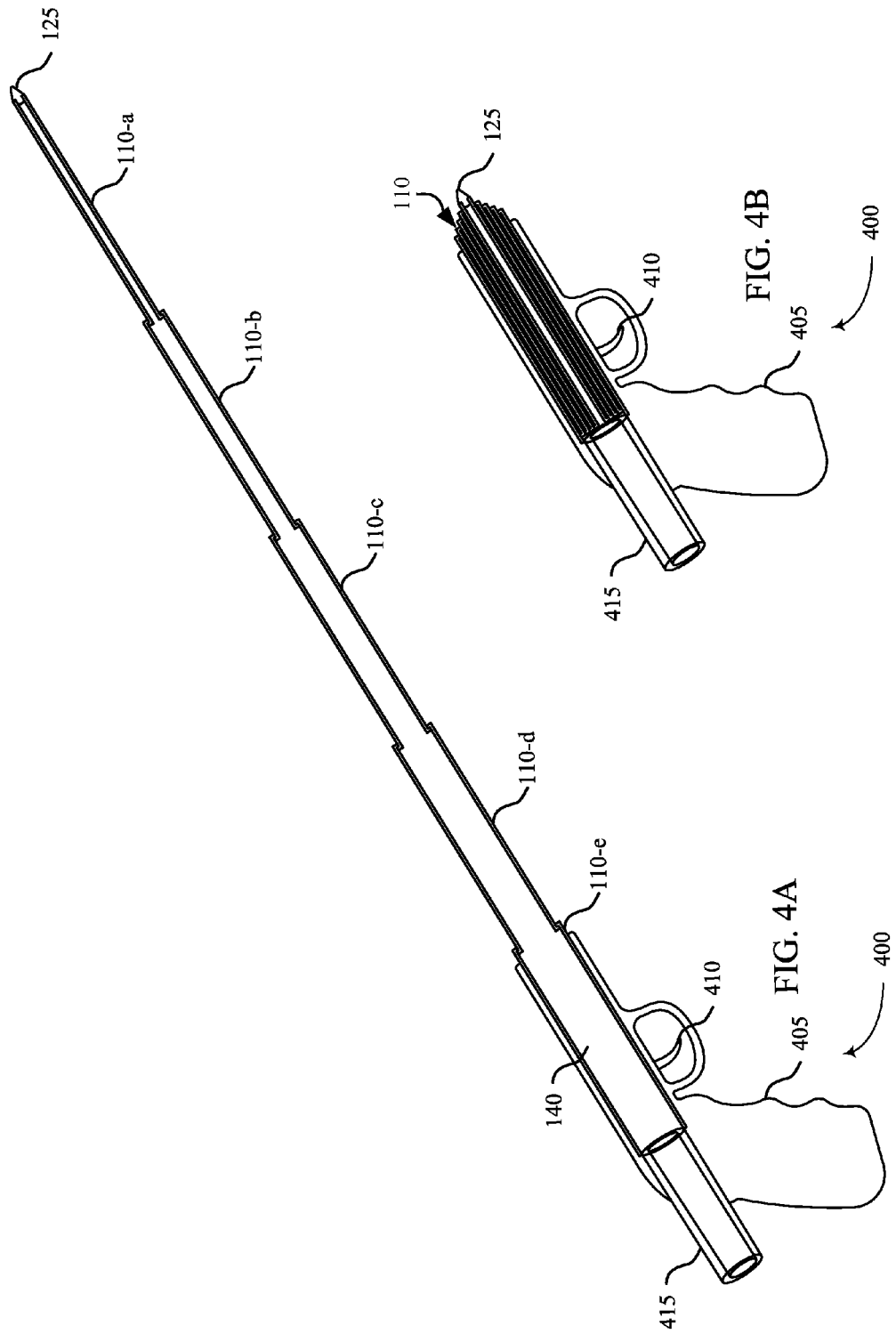
FIG. 4A illustrates an example of a breathing apparatus in an expanded configuration in accordance with aspects of the present disclosure.
FIG. 4B illustrates an example of a breathing apparatus in a collapsed configuration in accordance with aspects of the present disclosure.

FIG. 4A illustrates an example of a breathing device 400 in an expanded configuration in accordance with aspects of the present disclosure. FIG. 4B illustrates an example of the breathing device 400 in a collapsed configuration in accordance with aspects of the present disclosure. The breathing device 400 may be an example of the breathing devices or may include features of the breathing devices 100, 200, or 300 described with reference to FIGS. 1, 2, and 3. The breathing device 400 may include a pistol-shaped handle 405. The handle 405 may facilitate gripping and manipulation of the breathing device 400, especially when the user is buried in snow. The handle 405 may also include a trigger 410. As described in more detail below, the trigger 410 may be configured to release or otherwise cause the extension of the tubular members 110, thereby transition the device from the collapsed configuration to the expanded configuration.

The breathing device 400 may also include a breathing port 415. As described above, the breathing port 415 may provide air access to the internal lumen 140 that connects the breathing port 415 to a plurality of apertures (not shown here for clarity) at or near the distal end of the breathing device 400. The breathing port 415 may include a flexible or stiff tube that extends away from the handle 405. The length of the breathing port 415 may be adjustable so as to reach from the mouth of the user to where the user is holding the breathing device 400.

Figure 5:
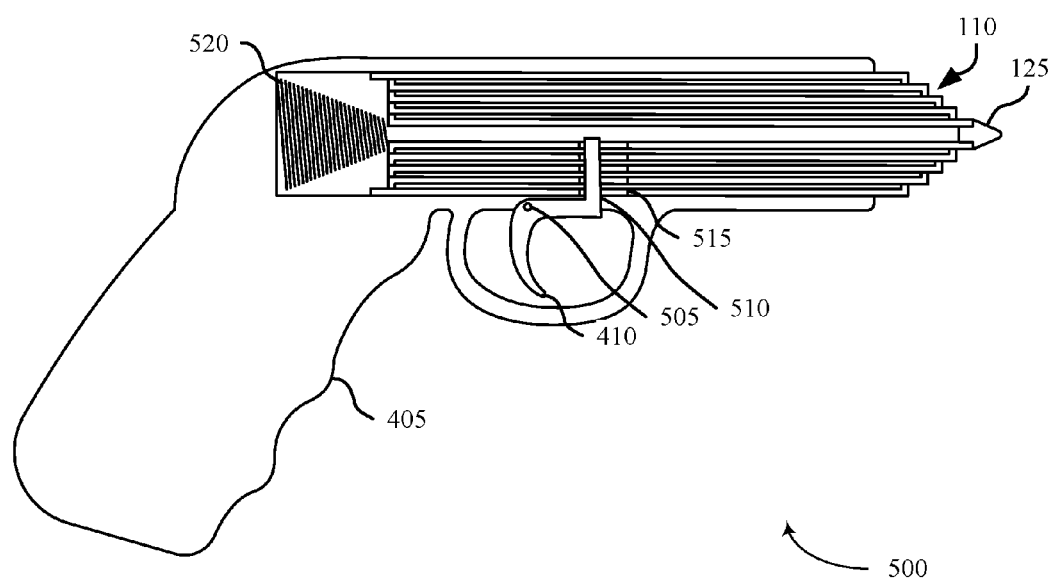
FIG. 5 illustrates an example of a breathing apparatus in a collapsed configuration in accordance with aspects of the present disclosure.

FIG. 5 illustrates an example of a breathing device 500 in a collapsed configuration in accordance with aspects of the present disclosure. The breathing device 500 may be an example of the breathing devices or may include features of the breathing devices 100, 200, 300, or 400 described with reference to FIGS. 1, 2, 3, and 4.

The breathing device 500 may include a spring 520, which may be an example of spring assembly 205 as described with reference to FIG. 2. The breathing device 500 may also include a trigger 410 that is configured to release the tubular members 110 so that the spring 520 can extend the tubular members 110 in a telescoping manner as described above. The trigger 410 may be coupled to the handle 405 and configured to pivot about a pin 505. The trigger 410 may also include a latch portion 510. In some examples, each of the tubular members 110 may have a hole or notch cut out so as to form a continuous tunnel feature 515 when the tubular members 110 are in the collapsed configuration. The latch portion 510 may be sized to extend at least all the way through the tunnel feature 515 and engage the inner-most tubular member 110.

The trigger 410 may be held in place by a spring or some other latching mechanism (e.g., a safety switch). To release the tubular members, the user may pull on the trigger, which will cause the latch portion 510 to pull down through the tunnel feature 515. As the latch portion 510 is pulled down through the tunnel feature 515, the inner most tubular member 110 (e.g., tubular member 110-a illustrated with respect to FIG. 4A) is no longer restrained by the latch portion 510. Accordingly, the inner most tubular member 110 is free to extend distally due to the compression force of spring 520. Similarly, as the latch portion 510 becomes disengaged from the second inner most tubular member 110 (e.g., tubular member 110-b illustrated with respect to FIG. 4A), that tubular member 110 will be free to extend distally. In use, once the trigger 410 is pulled, the tubular members 110 will be released nearly simultaneously, allowing the breathing device 500 to telescope to a fully extended configuration as described above.

Figure 6:
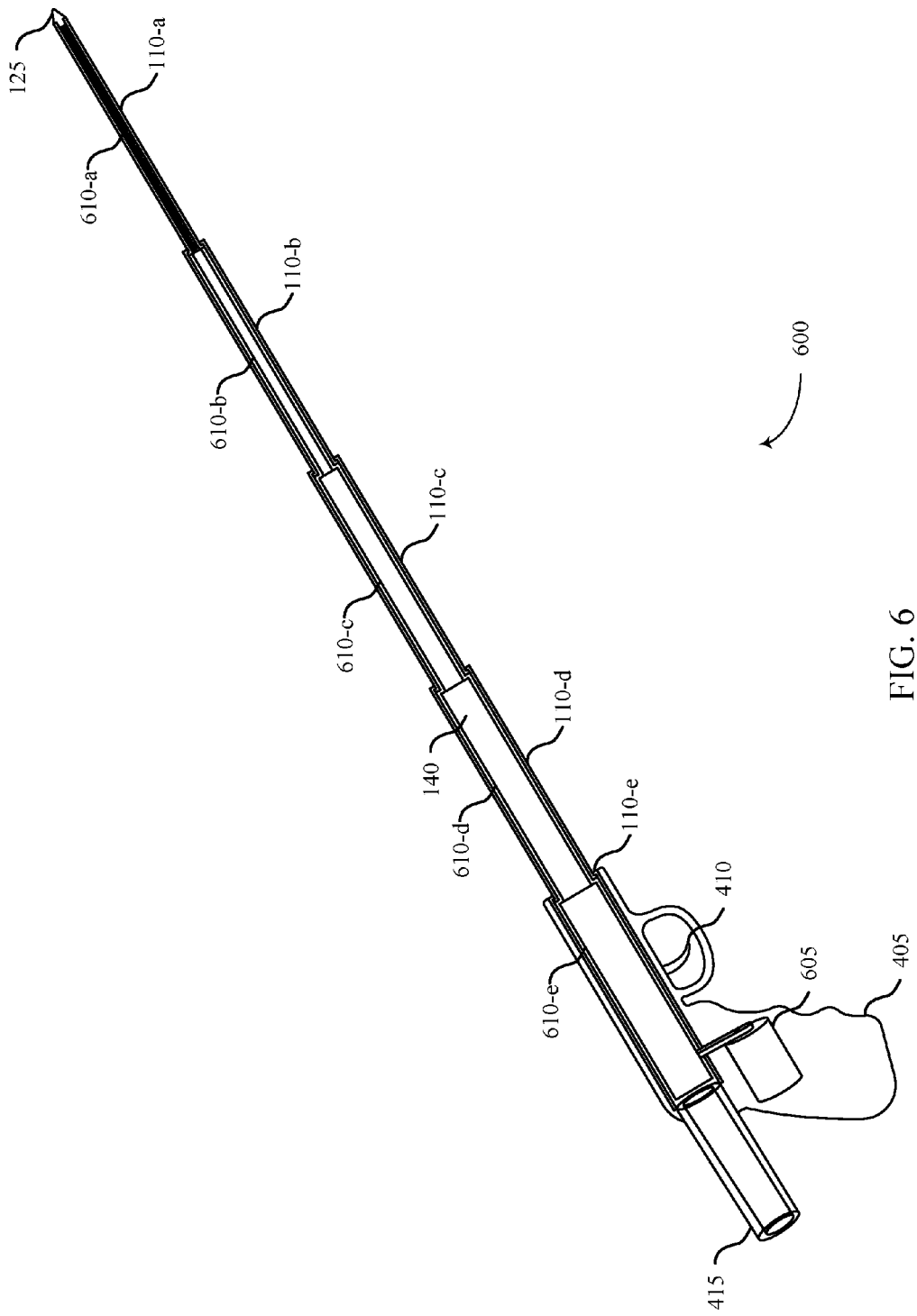
FIG. 6 illustrates an example of a breathing apparatus with a motorized extension device in an expanded configuration in accordance with aspects of the present disclosure.

FIG. 6 illustrates an example of a breathing device 600 in an expanded configuration in accordance with aspects of the present disclosure. The breathing device 600 may be an example of the breathing devices or may include features of the breathing devices 100, 200, 300, 400, or 500 described with reference to FIG. 1, 2, 3, 4, or 5. Breathing device 600 may include a motorized extension mechanism disposed within the body of the breathing device. The motorized extension mechanism may be used instead of or in addition to the springs and spring assemblies described above to extend the tubular members 110.

In some examples, the motorized extension mechanism may include a motor 605 that powers a linear actuator that includes actuator members 610-a, 610-b, 610-c, 610-d, and 610-e. The actuator members 610 may be sized to generally fit within a corresponding tubular member 110. In a collapsed configuration, the actuator members 610 may be collapsed in a telescoping manner similar to the tubular members 110. In response to pulling the trigger 410 (or some other triggering mechanism such as pushing a button, etc.), the motor 605 may cause the actuator members 610 to extend distally, thereby causing the tubular members 110 to extend distally. The motor 605 may be powered by a local power source such as a battery.

In other examples, instead of a motorized extension mechanism, the breathing device 600 may include a chamber of compressed air (e.g., nitrogen or carbon dioxide) configured to extend the tubular members 110 once triggered. For example, the motor 605 may be replaced by a chamber of compressed air and the actuator members 610 may be replaced by an internal bladder sized to run the length of the breathing device 600 when expanded. The trigger 410 may be configured to release the compressed air into the bladder when pulled, thereby allowing the bladder to fill up and extend the tubular members 110 distally.

It may be appreciated that other devices, assemblies, or methods may be used to extend the tubular members 110 from a collapsed configuration to an expanded configuration as described herein without departing from the scope of the present disclosure. Also, it should be noted that the methods described above describe possible implementations, and that the operations and the steps may be rearranged or otherwise modified and that other implementations are possible.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block or simplified form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A breathing apparatus, comprising:
    a telescoping body configured to transition between a collapsed configuration and an expanded configuration, the body comprising a distal end, a proximal end, and a plurality of tubular members, wherein the plurality of tubular members are concentrically arranged and slidably coupled with respect to each other, and wherein a first tubular member of the plurality of tubular members comprises an inward-facing lip disposed on a distal end of the first tubular member and an outward-facing lip disposed on a proximal end of the first tubular member, wherein the inward-facing lip is configured to engage with an outward-facing lip of a second tubular member of the plurality of tubular members and prevent the second tubular member from distally sliding completely from the first tubular member as the body transitions from the collapsed configuration to the expanded configuration;
    a breathing port disposed on the proximal end of the body;
    a plurality of apertures disposed on a circumferential surface at least one of the plurality of tubular members;
    a lumen extending through the body and fluidly coupling the breathing port with the plurality of apertures, such that air flows from outside the breathing apparatus, through the plurality of apertures, through the lumen, through the breathing port, and to a user of the breathing apparatus;
    a sharpened tip disposed on the distal end of the body, wherein the sharpened tip comprises a conical body, and wherein an outer surface of the conical body consists of a smooth surface;
    a spring assembly disposed within the body and configured to extend the plurality of tubular members distally with respect to each other thereby extending the body from the collapsed configuration to the expanded configuration, the spring assembly comprising a plurality of compression springs;
    a handle member disposed on the proximal end of the body; and
    a trigger pivotably coupled with the handle member, wherein the trigger comprises a latch portion that extends through a wall of each of the plurality of tubular members, the latch portion configured to retain the plurality of tubular members in the collapsed configuration until the user pivots the trigger thereby withdrawing the latch portion through the wall and away from each of the plurality of tubular members.

2. The apparatus of claim 1, wherein the plurality of compression springs comprises a plurality of conically tapered compression springs.

3. The apparatus of claim 2, wherein the plurality of conically tapered compression springs are joined together to form a single conically tapered compression spring.

4. The apparatus of claim 3, wherein the plurality of conically tapered compression springs are threaded together.

5. The apparatus of claim 1, wherein the plurality of compression springs comprises a plurality of cylindrical compression springs.

6. The apparatus of claim 5, wherein a diameter of each of the plurality of cylindrical compression springs is different than a diameter of all the other of the plurality of cylindrical compression springs, and wherein the plurality of cylindrical compression springs are joined together to form a single conically tapered compression spring.

7. The apparatus of claim 5, wherein all but one of the plurality of tubular members comprises an internal ledge at a proximal end of the tubular member, and wherein one of the plurality of cylindrical compression springs is disposed within each of the all but one of the plurality of tubular members, and wherein each of the cylindrical compression springs abuts against the internal ledge of the corresponding tubular member within which it is disposed, and wherein the plurality of cylindrical compressing springs are separated from each other by at least the internal ledges of the tubular members.

8. The apparatus of claim 7, wherein a diameter of each of the plurality of cylindrical compression springs is selected to correspond to a diameter of the corresponding tubular member within which it is disposed.

9. The apparatus of claim 1, wherein a number of the plurality of compression springs is one less than a number of the plurality of tubular members.

10. The apparatus of claim 1, wherein the plurality of apertures are disposed on the circumferential surface of a distal-most tubular member of the plurality of tubular members.

11. The apparatus of claim 1, further comprising a dye pack disposed at the distal end of the body and configured to release dye when the body transitions from a collapsed configuration to an extended configuration.

12. The apparatus of claim 1, further comprising a global positioning system (GPS) beacon.

* * * * *